United States Patent
Hsieh et al.

(10) Patent No.: US 6,977,984 B2
(45) Date of Patent: Dec. 20, 2005

(54) METHODS AND APPARATUS FOR DYNAMICAL HELICAL SCANNED IMAGE PRODUCTION

(75) Inventors: Jiang Hsieh, Brookfield, WI (US); Eugene Clifford Williams, Waukesha, WI (US); Thomas Louis Toth, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 75 days.

(21) Appl. No.: 10/680,688

(22) Filed: Oct. 7, 2003

(65) Prior Publication Data

US 2005/0074085 A1 Apr. 7, 2005

(51) Int. Cl.[7] ................................................. A61B 6/03
(52) U.S. Cl. ............................. 378/4; 378/15; 378/901
(58) Field of Search ............................... 378/4, 15, 20, 378/901

(56) References Cited

U.S. PATENT DOCUMENTS

| | | | |
|---|---|---|---|
| 5,073,911 A | * 12/1991 | Ozaki et al. | .................. 378/20 |
| 5,090,037 A | 2/1992 | Toth et al. | |
| 5,224,136 A | 6/1993 | Toth et al. | |
| 5,262,946 A | * 11/1993 | Heuscher | ..................... 378/15 |
| 5,377,250 A | * 12/1994 | Hu | .............................. 378/15 |
| 5,515,409 A | 5/1996 | Hsieh | |
| 5,891,030 A | * 4/1999 | Johnson et al. | ............. 600/407 |
| 6,038,278 A | 3/2000 | Hsieh et al. | |
| 6,185,271 B1 | * 2/2001 | Kinsinger | ..................... 378/19 |
| 6,298,112 B1 | 10/2001 | Acharya et al. | |
| 6,332,013 B1 | 12/2001 | Hsieh | |
| 6,381,297 B1 | 4/2002 | Hsieh | |
| 6,385,278 B1 | 5/2002 | Hsieh | |
| 6,404,842 B1 | 6/2002 | Hsieh | |
| 6,421,411 B1 | 7/2002 | Hsieh | |
| 6,452,996 B1 | 9/2002 | Hsieh | |
| 6,463,117 B1 | 10/2002 | Hsieh | |
| 6,490,334 B1 | 12/2002 | Wang et al. | |
| 6,522,714 B1 | 2/2003 | Wang et al. | |
| 6,529,576 B2 | 3/2003 | Hsieh et al. | |
| 6,597,803 B1 | 7/2003 | Pan et al. | |
| 6,600,802 B1 | 7/2003 | Hsieh | |
| 2003/0007604 A1 | 1/2003 | Hsieh et al. | |
| 2003/0171665 A1 | 9/2003 | Hsieh | |

* cited by examiner

*Primary Examiner*—Edward J. Glick
*Assistant Examiner*—Chih-Cheng Glen Kao
(74) *Attorney, Agent, or Firm*—Carl B. Horton, Esq.; Armstrong Teasdale LLP

(57) ABSTRACT

The present invention provides a method for producing images of an object. The method includes dynamically helically scanning an object on a moving table utilizing a scanning imaging system. During the scan, projection views of the object are acquired and stored together with corresponding table locations. A plane for reconstruction of an image of the object is selected. The stored table locations are used to determine geometric variables applicable to the stored projection views; and the stored projection views are filtered and backprojected utilizing the geometrical variables to reconstruct an image of the object at the reconstruction plane.

20 Claims, 4 Drawing Sheets

METHODS AND APPARATUS FOR DYNAMICAL HELICAL SCANNED IMAGE PRODUCTION

BACKGROUND OF THE INVENTION

This invention relates generally to scanning imaging systems, and more particularly to the production of images by scanning imaging systems having a table that is capable of moving at a variable rate during a scan of an object or a person.

Known scanning computed tomography (CT) imaging systems do not allow for the pitch of a helical scan to vary during a scan. Instead, the helical pitch (i.e., table speed) is held constant during a CT scan. To achieve constant table speed, the table is positioned a distance away from a desired starting location and accelerated to a desired speed. During the acceleration, the x-ray beam is not turned on and no data is acquired. When the table reaches the desired speed and passes the starting location, the beam is turned on and data acquisition starts.

Faster and higher performance scanning CT imaging systems allow for increased clinical applications. Several new clinical applications in the cardiac and perfusion areas require that a scanning CT imaging system vary its pitch while scanning. For example, a typical head perfusion requires coverage of 4–8 cm along the patient's axis (i.e., a z-axis of the imaging system, normally corresponding to a head-to-toe axis of a patient). Known multi-slice CT imaging systems are able to cover only 2 cm at any given instant. Thus, it would be advantageous to acquire the perfusion data in a shuttle mode in which the patient table is moving back and forth during scanning to cover the entire perfusion organ. A shuttle mode such as this requires that data acquisition and reconstruction occur during the ramping-up and ramping-down periods of table motion. Known scanning CT imaging systems do not provide this capability.

BRIEF DESCRIPTION OF THE INVENTION

Some configurations of the present invention thus provide a method for producing images of an object. The method includes dynamically helically scanning an object on a moving table utilizing a scanning imaging system. During the scan, projection views of the object are acquired and stored together with corresponding table locations. A plane for reconstruction of an image of the object is selected. The stored table locations are used to determine geometric variables applicable to the stored projection views; and the stored projection views are filtered and backprojected utilizing the geometrical variables to reconstruct an image of the object at the reconstruction plane.

Some other configurations of the present invention provide a method for producing images of an object that includes dynamically helically scanning an object on a moving table utilizing a scanning imaging system, acquiring and storing projection views of the object and, for only some of the acquired projection views, corresponding determined or estimated table locations. A plane for reconstructing an image of the object is selected and geometric variables applicable to the stored projection views are determined utilizing the stored table locations. The stored projection views are filtered and backprojected utilizing the geometrical variables to reconstruct an image of the object at the reconstruction plane.

Still other configurations of the present invention provide an imaging apparatus configured to dynamically helically scan an object on a moving table. The apparatus is further configured to acquire and store projection views of the object and corresponding table locations, utilize stored table locations to determine geometric variables applicable to the stored projection views; and filter and backproject the stored projection views utilizing the geometrical variables to reconstruct an image of the object at a selected reconstruction plane.

Other configurations of the present invention also provide an imaging apparatus configured to dynamically helically scan an object on a moving table. The imaging apparatus is further configured to acquire and store projection views of the object and, for only some of the acquired projection views, corresponding determined or estimated table locations. Also, the imaging apparatus is configured to utilize stored table locations to determine geometric variables applicable to the stored projection views, and filter and backproject the stored projection views utilizing the geometrical variables to reconstruct an image of the object at a selected reconstruction plane.

Various configurations of the present invention allow an exact, or nearly exact table location to be used in the image reconstruction process. These configurations are useful, for example, for varying the velocity or acceleration of a patient during a helical scan to meet clinical requirements. Applications of the invention include, but are not limited to, cardiac scanning applications and perfusion applications. Moreover, the ability to start a helical scan during acceleration and/or deceleration of the patient table can be provided when scanning at a fixed helical pitch.

DETAILED DESCRIPTION OF THE INVENTION

Figure 1:
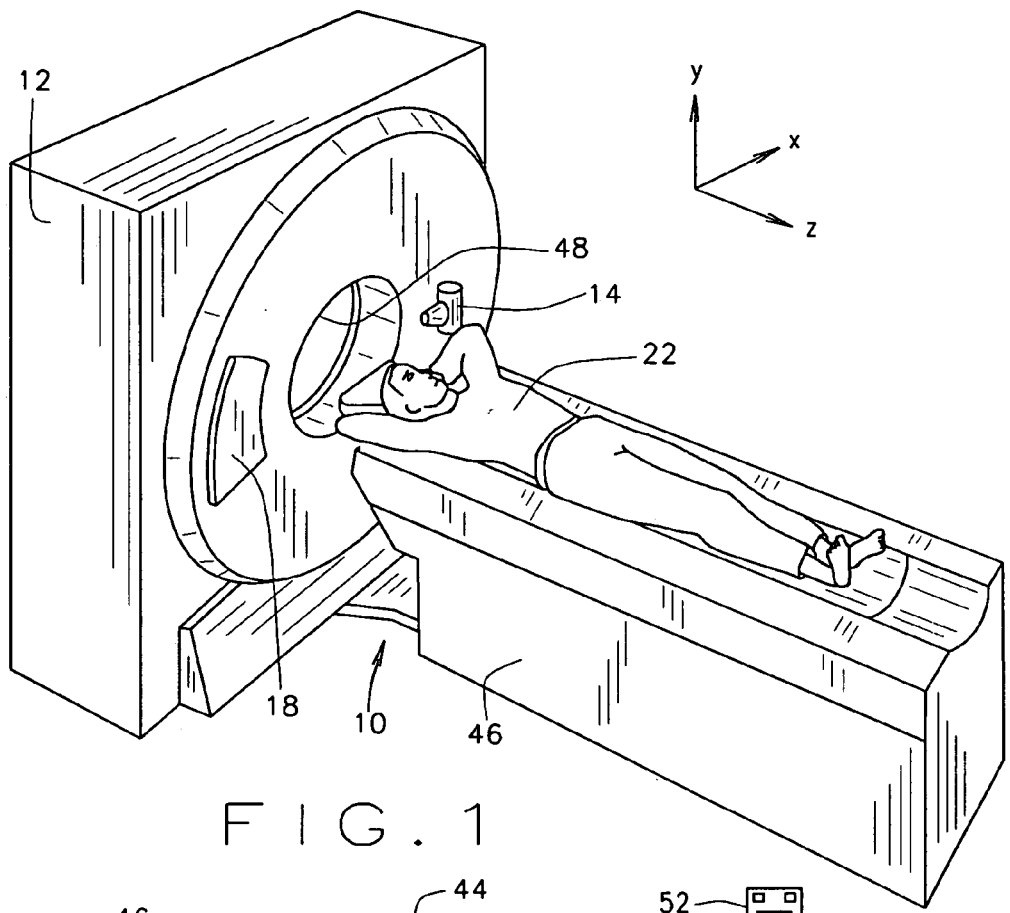
FIG. 1 is a pictorial view of a CT imaging system

It will be appreciated that a technical effect of the configurations of the present invention described herein is the scanning and reconstruction of an object or patient utilizing a dynamical helical scan.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Further as used herein, the term "dynamical helical scan" refers to a helical scan in which data is collected while the pitch of the scan varies. More particularly, in configurations of the present invention, a table holding an object during a scan is accelerated or decelerated while a scan is taking place to produce a variable pitch scan. For purposes of the present invention, it does not matter whether the acceleration or deceleration is intentional, incidental, or entirely unintentional, although in the configurations described herein, it is intentional. In some intentional cases of acceleration or deceleration, a feedback loop is used to adjust table speed during a scan.

In some configurations of the present invention, the pitch of a scan is a variable in the sense that the location of the x-ray tube and detector relative to an image reconstruction plane is determined using a measured or estimated table position. In these configurations, the table can move at a constant speed for part or all of a scan, but it is not constrained to do so as in a constant pitch scan. Unless otherwise specifically noted, scans in which the pitch of a scan is a variable in the above sense are intended to be included within the scope of the term "dynamical helical scan."

Furthermore, configurations of the present invention described herein have a constant gantry rotation speed during data collection, although a constant gantry rotation speed is not required to practice the present invention.

Figure 2:
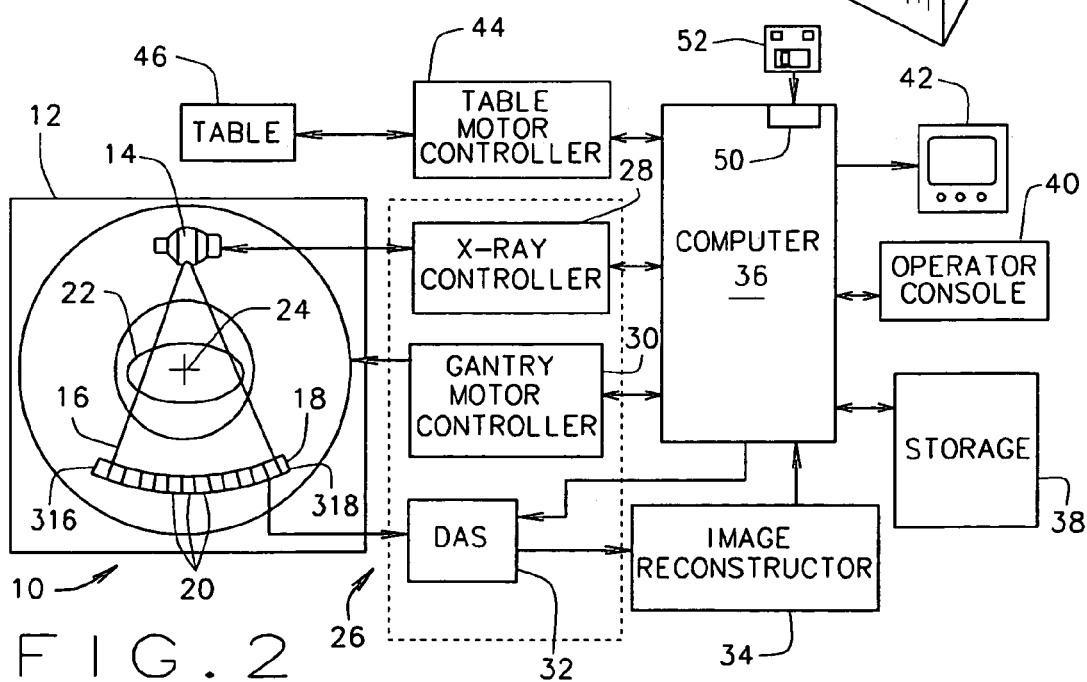
FIG. 2 is a block schematic diagram of the system illustrated in FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray tube 14 (also called x-ray source 14 herein) that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40, that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector-rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, the benefits of the invention can also accrue to non-medical imaging systems such as those systems typically employed in an industrial setting or a transportation setting. An example of such an imaging system includes, but is not limited to, a baggage scanning system for an airport or other transportation center.

Some configurations of the present invention permit helical pitch to vary during a scan. Such scans are referred to herein as "dynamical helical scans." These configurations accurately determine or estimate the location of an object or patient 22 in a z-direction and include or store that position data with the acquired CT raw image data. In these configurations, a location of table 46 is reported at a frequency determined in accordance with accuracy requirements and practicality.

More particularly, in some configurations, a location of table 46 location reported with every projection sample of a dynamical helical scan, i.e., every protection view is acquired with attenuation information and table 46 location. However, for many uses that could advantageously use a dynamical helical scan mode, the speed and accuracy of position encoders (not shown) in many known CT imaging systems 10 is insufficient to meet the rigorous requirements that this degree of position reporting would require. Thus, other configurations of the present invention report the location of table 46 every Nth view, where N is selected in accordance with table 46 acceleration and deceleration characteristics, or predetermined (i.e., selected in advance). In configurations in which acceleration and deceleration are sufficiently smooth, the value of N can be large. In configurations in which acceleration and deceleration have significant high frequency components, the value of N should be smaller.

The selection of estimation algorithms used to estimate table 46 position can also affect the range of N that is practical. For example, to estimate intermediate locations between two measured locations, some configurations utilize linear interpolation or higher order interpolation (such as Lagrange interpolation). Higher order interpolation allows for significant nonlinearity while maintaining estimation accuracy. After interpolation, the location of table 46 is generated for each projection view. In some configurations, to accomplish some types of interpolation, and most particularly to accomplish nonlinear interpolation, the value of N is changed during a scan. By way of example only, if a counter J is used to count scans and the first value of N is 8, a first table position may be recorded J=8, followed by J being reset to 1 and N being changed to 5. The second table position would then be recorded when J=5, followed by J being reset to 1 and N being changed to 6, etc.

Image reconstruction uses raw image data together with the z-axis location (or synonymously, "z location") of object or patient 22 to reconstruct an image at a user-defined location (i.e., a user defined "slice" or image reconstruction plane of object or patient 22). The reconstruction process in some configurations includes an adjustment of the back backprojection process. More particularly, for dynamical helical scanning in configurations of the present invention, the location of x-ray tube 14 and detector 18 relative to the image reconstruction plane is calculated in accordance with a measured or estimated location of table 46. This location information is input to the backprojection process to ensure that each x-ray path is accurately determined.

In addition to using measured or estimated locations of table 46 in determining each x-ray path, some configurations of the present invention also normalize the contribution of projection samples to each pixel of the reconstructed image. In configurations of the present invention, weights for dynamical helical scans are determined as the scan is performed. These determined weights are used to weight redundant data in a manner that avoids shading and/or streaking artifacts. (For constant pitch helical scans, the location of each projection sample can be determined before the start of a scan, allowing-weights to be determined in advance of a scan.)

For example, for each image location, a center view is determined utilizing the location of gantry 12 for the view. In general, the amount of attenuation data available for the reconstruction of a particular image is more than the minimum halfscan requirement. Therefore, in some configurations, the center view location (rather than the image reconstruction location) is changed, and a set of weights produced for a different projection set. This process is repeated in some configurations to ensure that all projections that contribute to the imaging plane are used. The halfscan weights are then properly weighted and summed to produce a final helical weight.

In some configurations of the present invention, the number of projection views that have contributed to each pixel location in an image is determined. Once the number of projections is sufficient to satisfy the requirements for a full reconstruction, the contribution of additional projections, if any, are eliminated to avoid redundancy.

In many configurations of the present invention, one or more image planes are reconstructed at the same time that the table is moving and data is being collected during a scan. The pipelining of processes is well known to those in the art, as is the reordering of processes in which the input of one is not dependent in time or value upon the output of the other. Thus, it is believed that the added complexity that would be required for the description of a pipelined configuration would hinder a straightforward description of the present invention. As a result, for simplicity of explanation, many of the configurations described herein collect view data during a scan and reconstruct only one image at a preselected image plane after the scan has completed and the table motion has terminated.

In addition, there are many ways in which iterative loops may be implemented. Variations include initializing a loop variable to 1 and counting up to a limit, initializing the loop variable to the limit and counting down to 1, initializing the loop variable to 0 instead of 1, testing at the top of the loop rather than the bottom (or vice versa), etc. "Bookkeeping" details such as which loop implementation to use can be left as a design choice to one skilled in the art. Certain other details fit into a category best described as "end effects." End effects include details such as whether it is necessary or desirable to record the position of table 46 for the first view (rather than for the first time at the Nth view) and/or for the final view, even if the final view is not an "Nth view." The handling of such end effects can also be left as a design choice to one skilled in the art.

Also, it will be recognized that the table 46 location information made available in configurations of the present invention is used by computer 36 and/or image reconstructor 34 to determine geometric variables used in the weighting, normalization, filtering, and backprojection processes. One of ordinary skill in the art would understand the design choices necessary to configure imaging system 10 to utilize table 46 location information to determine these variables. Moreover, the invention does not restrict other design choices, such as the choice of weighting function to use. For example, nothing restricts a configuration from providing, or having available as a selection, one or more different weighting functions.

Figure 3:
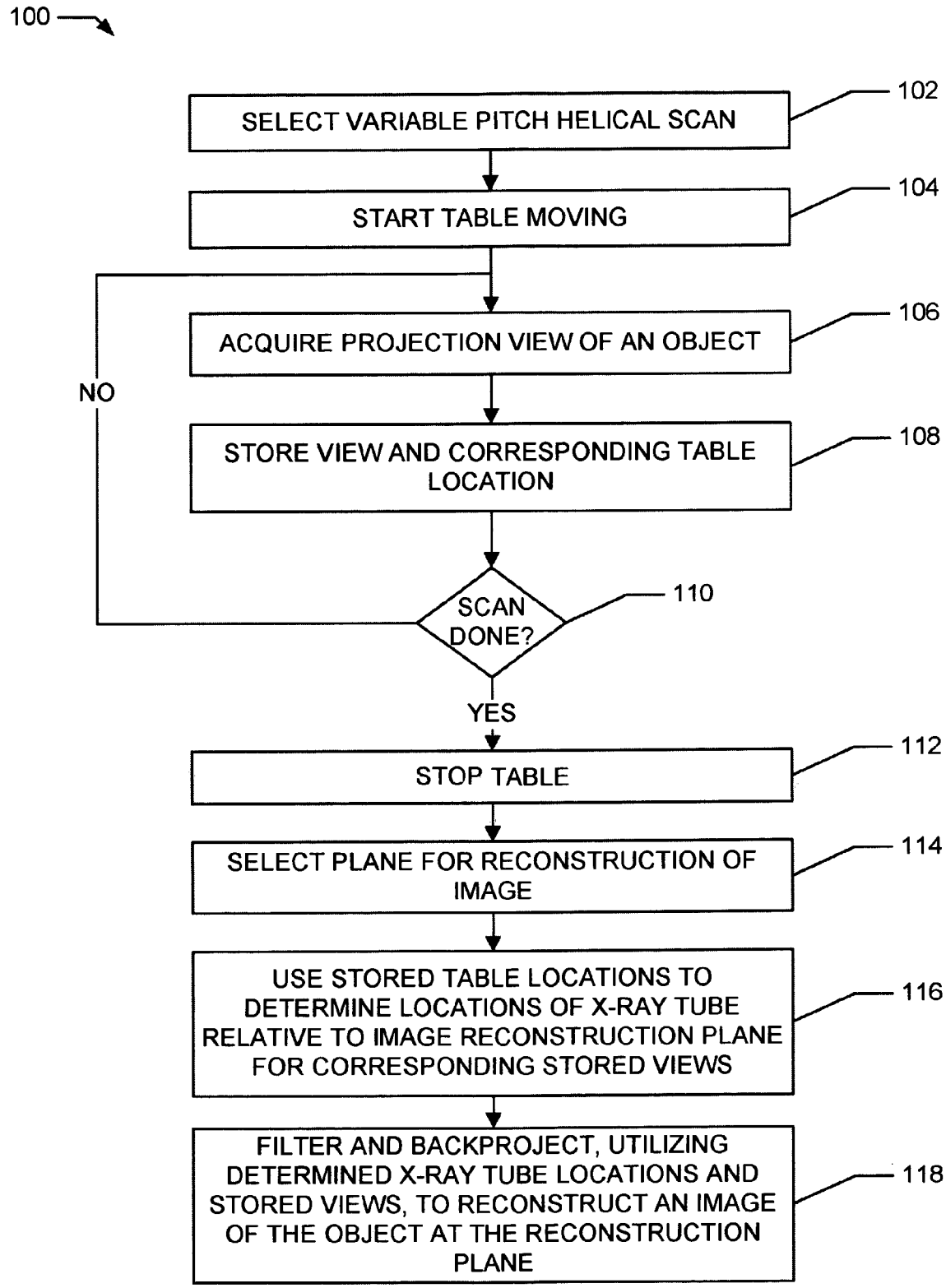
FIG. 3 is a flow chart representative of scanning and image reconstruction performed in some configurations of the present invention that store table location with every acquired projection view.

With the foregoing caveats in mind and referring to FIG. 3, a flow chart 100 representative of some configurations of the present invention is shown. A technical effect of the processes of the present invention described by flow chart 100 is the scanning of an object or patient 22 and the generation of images thereof. Configurations of the present invention are permitted to pipeline the operations shown in flowchart 100, add additional operations, or alter the sequence of operations to any extent that it is logical and possible to do so to achieve the intended technical effect.

A dynamical helical scan type is selected at 102. (Selection 102 can be omitted in configurations that do not provide a selection of scan types other than dynamical helical scans.) The motion of table 46 is then started at 104, in accordance with the parameters of the dynamical scan. A projection view of an object or patient 22 being scanned on table 46 is acquired at 106. In configurations described by flowchart 100, the location of table 46 is determined for each such acquisition, and the view and corresponding table location are stored at 108. If the scan is not finished, the procedure returns to 106 to acquire another projection view. If the scan is finished, the motion of table 46 is stopped at 112 and a plane for the reconstruction of an image is selected at 114. At 116, the stored table locations are used to determine a location of x-ray tube 14 and detector 18 relative to the selected image reconstruction plane for each corresponding stored view. At 118, filtering and backprojecting are performed to reconstruct an image of object or patient 22 at the reconstruction plane, utilizing the determined x-ray tube and detector locations and the stored views.

In some configurations of the present invention and referring to FIG. 2 and FIG. 3, the locations of table 46 are reported back to computer 36 during the scan at 108 and the physical operations performed during a scan are controlled directly or indirectly by computer 36. Acquired data and table 46 locations are stored at 108 in storage device 38. The selection of a dynamical helical scan at 102 and/or the selection of an image location or reconstruction plane can be performed by an operator, using operator console 40 and display 42 to make the selection. Otherwise, the selection of the helical scan and/or the selection of an image location or reconstruction plane may be performed automatically by computer 36. (Many pipelined configurations automatically or manually select a plurality of image locations or reconstruction planes for each scan and use views already acquired and stored to reconstruct images of the object or patient while other views for other images are being acquired and stored.) The determination of locations at 116 is performed by computer 36 utilizing data stored in storage device 38, and the filtering and backprojecting is performed by image reconstructor 34. Other configurations are permitted to divide the above-described functions differently amongst the various components of imaging system 10.

Figure 4:
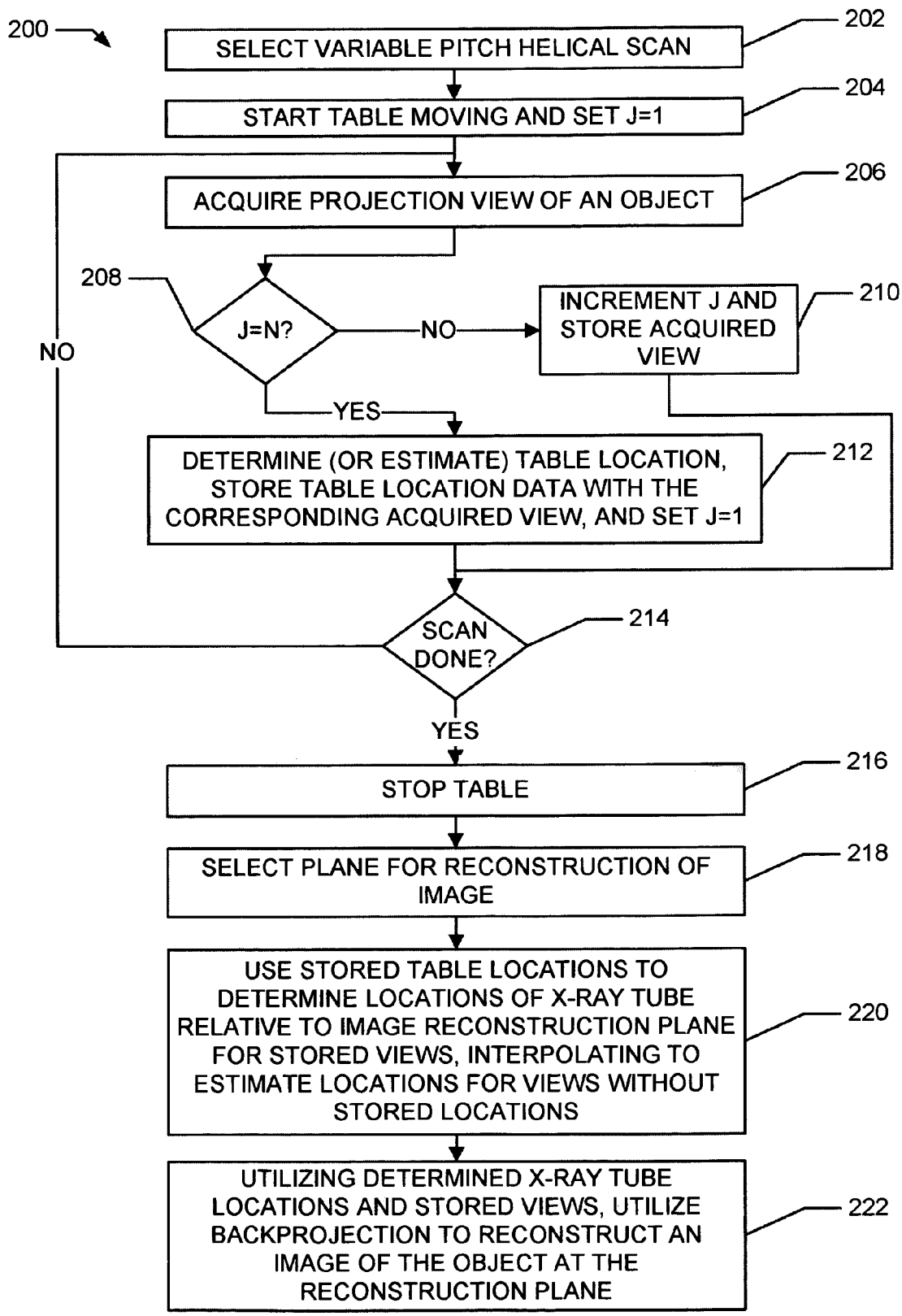
FIG. 4 is a flow chart representative of scanning and image reconstruction performed in some configurations of the present invention that store table location with only some acquired projection views.

Referring to FIG. 4, another flow chart 200 representative of some configurations of the present invention is shown. A technical effect of the processes of the present invention described by flow chart 200 is the scanning of an object or patient 22 and the generation of images thereof. Configurations of the present invention are permitted to pipeline the operations shown in flowchart 200, add additional operations, or alter the sequence of operations to any extent that it is logical and possible to do so to achieve the intended technical effect.

A dynamical helical scan type is selected at 202. (Selection 202 can be omitted in configurations that do not provide a selection of scan types other than dynamical helical scans.) The motion of table 46 is then started at 204, in accordance with the parameters of the dynamical scan, and a loop variable J is initialized. A projection view of an object or patient 22 being scanned on table 46 is acquired at 206. In configurations described by flowchart 200, the location of table 46 is determined only for every Nth acquisition. Therefore, a test is performed at 208 to determine whether to determine the location of table 46 for this acquisition. If no location is to be stored, the looping variable is incremented and the acquired view is stored at 210. Otherwise, the location of table 46 is determined (or estimated), the location is stored with the corresponding acquired view at 212, and the looping variable is reinitialized. In either case, a test is then performed to determine whether the scan is finished at 214. If not, another projection view of an object is acquired at 206. Otherwise, the table is stopped at 216 and a plane for reconstructing an image is selected at 218. The stored table 46 locations are used to determine the location of x-ray tube 14 and detector 18 for the stored views relative to the image reconstruction plane at 220. For stored views for which a corresponding table location was not stored at 212, a table location is estimated using an interpolation. At 222, filtering and backprojecting are performed to reconstruct an image of object or patient 22 at the reconstruction plane, utilizing the determined and/or interpolated x-ray tube and detector locations and the stored views.

Figure 5:
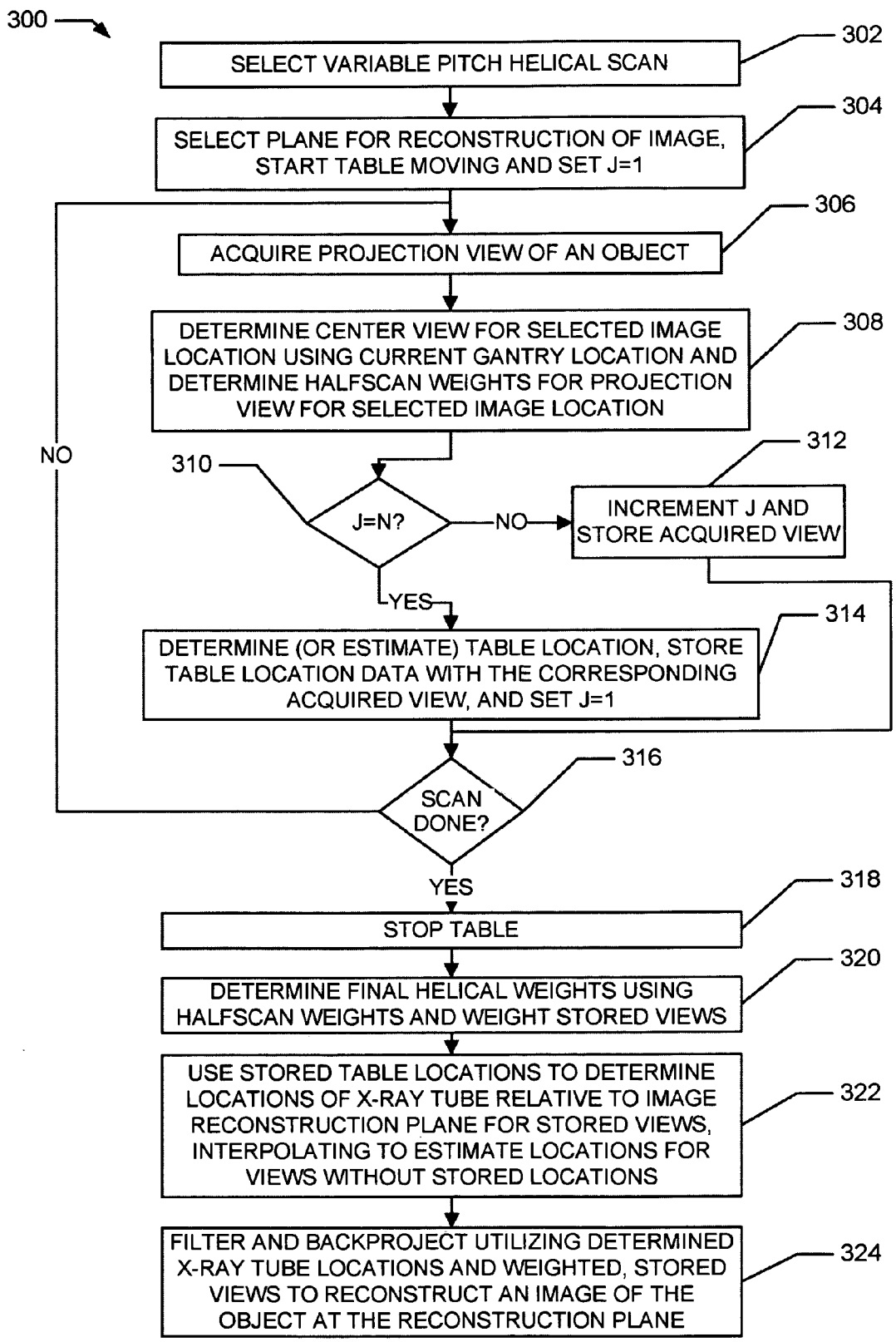
FIG. 5 is a flow chart representative of scanning and image reconstruction performed in some configurations of the present invention that store table location with only some acquired projection views and which also weight the acquired views to avoid shading and/or streaking artifacts in reconstructed images.

Referring to FIG. 5, another flow chart 300 representative of some configurations of the present invention is shown. A technical effect of the processes of the present invention described by flow chart 300 is the scanning of an object or patient 22 and the generation of images thereof. Configurations of the present invention are permitted to pipeline the operations shown in flowchart 300, add additional operations, or alter the sequence of operations to any extent that it is logical and possible to do so to achieve the intended technical effect.

A dynamical helical scan type is selected at 302. (Selection 302 can be omitted in configurations that do not provide a selection of scan types other than dynamical helical scans.) The motion of table 46 is then started at 304, in accordance with the parameters of the dynamical scan, and a loop variable J is initialized. A projection view of an object or patient 22 being scanned on table 46 is acquired at 306. A center view for a selected image location is determined at 308 using the current gantry 12 location, halfscan weights are determined for the projection view for the selected image location at 308. In configurations described by flowchart 300, the location of table 46 is determined only for every Nth acquisition. Therefore, a test is performed at 310 to determine whether to determine the location of table 46 for this acquisition. If no location is to be stored, the looping variable is incremented and the acquired view is stored at 312. Otherwise, the location of table 46 is determined (or estimated), the location is stored with the corresponding acquired view at 314, and the looping variable is reinitialized. In either case, a test is then performed to determine whether the scan is finished at 316. If not, another projection view of an object is acquired at 306. Otherwise, the table is stopped at 318. Final helical weights are determined utilizing the halfscan weights determined at 308 and the stored views are weighted using the final helical weights at 320. The stored table locations are used to determine the location of x-ray tube 14 and detector 18 for stored views relative to the image reconstruction plane at 322, using interpolation to estimate table 46 locations for those views for which no table location data was stored at 314. Filtering and backprojecting is then performed on the weighted views to reconstruct an image of the object at the reconstruction plane at 324. This filtering and backprojecting utilizes the x-ray tube 14 and detector 18 positions determined at 322.

It will be appreciated that various configurations of the present invention allow an exact, or nearly exact table location to be used in the image reconstruction process, so that the velocity or acceleration of a patient during a helical scan can be varied to meet clinical requirements. This capability is particularly useful for enhancing applications that include, but are not limited to, cardiac scanning applications and perfusion applications. Moreover, the ability to start a helical scan during acceleration and/or deceleration of the patient table is provided when scanning at a fixed helical pitch.

Configurations of the present invention are not limited to Computed Tomography (CT). Other imaging modalities, such as Magnetic Resonance (MR), can be used to acquire images with a dynamically changing table speed.

Also, various dynamic scans described in examples disclosed herein are performed in an "open loop" manner. However, configurations of the present invention can include a feedback to adjust table speed during a scan. For example, based on measured projections and/or other information, helical pitch can be adjusted to obtain improved or optimum clinical results, such as maximum contrast enhancement. An example of such a configuration would provide an additional function between blocks 108 and 110 of FIG. 3 that compares the current table location to a desired table location and adjusts the movement of the table in a compensating manner. A similar function can be added, for example, immediately before block 214 of FIG. 4 (irrespective of whether block 214 is reached via block 210 or block 212), or immediately before block 316 of FIG. 5 (irrespective of whether block 316 is reached via block 312 or 314). These examples are not intended as exhaustive of the many ways in which feedback may be added to adjust table speed during a scan.

While the invention has been described in terms of various specific embodiments, those skilled in the art will recognize that the invention can be practiced with modification within the spirit and scope of the claims.

What is claimed is:

1. A method for producing images of an object comprising:
    dynamically helically scanning an object on a moving table utilizing a scanning imaging system;
    acquiring and storing projection views of the object and, for only some of the acquired projection views, corresponding determined or estimated table locations;
    selecting a plane for reconstruction of an image of the object;
    utilizing stored table locations to determine geometric variables applicable to the stored projection views; and
    filtering and backprojecting the stored projection views utilizing the geometrical variables to reconstruct an image of the object at the reconstruction plane.

2. A method in accordance with claim 1 wherein the scanning imaging system is a magnetic resonance imaging system.

3. A method in accordance with claim 1 wherein the scanning imaging system is a computed tomographic imaging system.

4. A method in accordance with claim 1 wherein said utilizing stored table locations to determine geometric variables applicable to the stored projection views comprises utilizing interpolation to estimate table locations between stored projection views lacking a corresponding determined or estimated table location.

5. A method in accordance with claim 4 wherein said interpolation is a linear interpolation.

6. A method in accordance with claim 4 wherein said interpolation is a nonlinear interpolation.

7. A method in accordance with claim 1 wherein said geometric variables include a location of an x-ray tube and detector relative to the image reconstruction plane.

8. A method in accordance with claim 7 wherein the scanning imaging system is a computed tomographic imaging system having a rotating gantry, and said method further comprises:
    determining a center view for a selected image location for the projection views utilizing gantry locations of the projection views;
    determining a weight for each projection view for the selected image location;
    determining final helical weights using the determined weights for each projection view; and
    weighting the stored projection views utilizing the determined final helical weights;
    and further wherein filtering and backprojecting the stored projection views comprises filtering and backprojecting the weighted stored projection views.

9. A method in accordance with claim 8 wherein said determining a weight for each projection view comprises determining a halfscan weight for each projection view.

10. A method in accordance with claim 1 further comprising utilizing feedback to adjust table speed during the dynamical helical scan.

11. An imaging apparatus configured to:
    dynamically helically scan an object on a moving table;

acquire and store projection views of the object and, for only some of the acquired projection views, corresponding determined or estimated table locations;

utilize stored table locations to determine geometric variables applicable to the stored projection views; and filter and backproject the stored projection views utilizing the geometrical variables to reconstruct an image of the object at a selected reconstruction plane.

12. An apparatus in accordance with claim 11 wherein said apparatus is a magnetic resonance imaging system.

13. An apparatus in accordance with claim 11 wherein said apparatus is a computed tomographic imaging system.

14. An apparatus in accordance with claim 11 wherein to utilize stored table locations to determine geometric variables applicable to the stored projection views, said apparatus is configured to utilize interpolation to estimate table locations between stored projection views lacking a corresponding determined or estimated table location.

15. An apparatus in accordance with claim 14 wherein said interpolation is a linear interpolation.

16. An apparatus in accordance with claim 14 wherein said interpolation is a nonlinear interpolation.

17. An apparatus in accordance with claim 11 further comprising an x-ray tube and a detector, and wherein said geometric variables include a location of said x-ray tube and said detector relative to the image reconstruction plane.

18. An apparatus in accordance with claim 17 wherein said apparatus is a computed tomographic imaging system having a gantry configured to rotate said x-ray tube and said detector around said object, said apparatus further configured to:

determine a center view for a selected image location for the projection views utilizing gantry locations of the projection views;

determine a weight for each projection view for the selected image location;

determine final helical weights using the determined weights for each projection view; and weight the stored projection views utilizing the determined final helical weights;

and further wherein to filter and backproject the stored projection views, said apparatus is configured to filter and backproject the weighted stored projection views.

19. An apparatus in accordance with claim 18 wherein to determine a weight for each projection view, said apparatus is configured to determine a halfscan weight for each projection view.

20. An apparatus in accordance with claim 11 further configured to utilize feedback to adjust table speed during the dynamical helical scan.

* * * * *